US012797402B2

(12) United States Patent
Cuenoud et al.

(10) Patent No.: US 12,797,402 B2
(45) **Date of Patent: *Nov. 17, 2026**

(54) COMPOSITIONS AND METHODS USING A NICOTINAMIDE ADENINE DINUCLEOTIDE (NAD+) PRECURSOR AND AT LEAST ONE KETONE OR KETONE PRECURSOR

(71) Applicant: SOCIETE DES PRODUITS NESTLE S.A., Vevey (CH)

(72) Inventors: Bernard Cuenoud, Cully (CH); India C. Severin, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 1081 days.

This patent is subject to a terminal disclaimer.

(21) Appl. No.: 17/254,403

(22) PCT Filed: May 24, 2019

(86) PCT No.: PCT/EP2019/063425
§ 371 (c)(1),
(2) Date: Dec. 21, 2020

(87) PCT Pub. No.: WO2019/242982
PCT Pub. Date: Dec. 26, 2019

(65) Prior Publication Data

US 2021/0267251 A1 Sep. 2, 2021

Related U.S. Application Data

(60) Provisional application No. 62/688,045, filed on Jun. 21, 2018.

(51) Int. Cl.
*A61K 31/706* (2006.01)
*A23L 33/00* (2016.01)
(Continued)

(52) U.S. Cl.
CPC .......... *A61K 31/706* (2013.01); *A23L 33/125* (2016.08); *A23L 33/40* (2016.08);
(Continued)

(58) Field of Classification Search
CPC .. A61K 31/706; A61K 9/0056; A61K 31/121; A61K 31/19; A61K 31/455; A23L 33/125; A23L 33/40; A23V 2002/00
See application file for complete search history.

(56) References Cited

U.S. PATENT DOCUMENTS 8,440,704 B2 5/2013 Lines
9,283,263 B2 3/2016 Westerlund et al.
(Continued)

FOREIGN PATENT DOCUMENTS

AU 2014298629 A1 2/2016
EP 0276559 A2 8/1988
(Continued)

OTHER PUBLICATIONS

Aragon et al., "Age-related muscle anabolic resistance: in evitable or preventable?", Nutrition Reviews, vol. 81(4):441-454, 2023. (Year: 2023).*

(Continued)

*Primary Examiner* — Kyung S Chang
(74) *Attorney, Agent, or Firm* — K&L Gates LLP

(57) ABSTRACT

A composition can treat or prevent at least one physical state selected from the group consisting of oxidative stress, a condition associated with oxidative stress, a reduced level of glutathione, and a condition associated with a reduced level of glutathione. The composition contains an effective amount of a combination of a Nicotinamide Adenine Dinucleotide (NAD+) precursor and at least one ketone or ketone precursor. The composition can be an enterally
(Continued)

ns if > 0.02 administered composition such as an orally administered food product or food supplement.

12 Claims, 2 Drawing Sheets

(51) Int. Cl.

| | |
|---|---|
| ***A23L 33/125*** | (2016.01) |
| ***A61K 9/00*** | (2006.01) |
| ***A61K 31/121*** | (2006.01) |
| ***A61K 31/19*** | (2006.01) |
| ***A61K 31/405*** | (2006.01) |
| ***A61K 31/4425*** | (2006.01) |
| ***A61K 31/455*** | (2006.01) |
| ***A61P 25/28*** | (2006.01) |

(52) U.S. Cl.
CPC .......... *A61K 9/0056* (2013.01); *A61K 31/121* (2013.01); *A61K 31/19* (2013.01); *A61K 31/455* (2013.01); *A61P 25/28* (2018.01); *A23V 2002/00* (2013.01)

(56) References Cited

U.S. PATENT DOCUMENTS

| | | | |
|---|---|---|---|
| 10,646,462 | B2 | 5/2020 | D'Agostino et al. |
| 10,952,982 | B2 | 3/2021 | Kirnon et al. |
| 2003/0158237 | A1 | 8/2003 | Saragovi et al. |
| 2009/0104171 | A1 | 4/2009 | Pardee et al. |
| 2009/0253781 | A1 | 10/2009 | Veech |
| 2014/0350105 | A1 | 11/2014 | D'Agostino et al. |
| 2016/0008325 | A1 | 1/2016 | Andrews et al. |
| 2016/0250169 | A1 | 9/2016 | Perez et al. |
| 2017/0204131 | A1 | 7/2017 | Szczepankiewicz et al. |
| 2018/0207190 | A1 | 7/2018 | Kim |
| 2018/0256612 | A1 | 9/2018 | Schmidt |
| 2018/0360975 | A1 | 12/2018 | Levin |
| 2019/0060336 | A1 | 2/2019 | Huizenga |

FOREIGN PATENT DOCUMENTS

| | | | |
|---|---|---|---|
| EP | 0726073 | A2 | 8/1996 |
| WO | 0185178 | | 11/2001 |
| WO | 2007001883 | | 1/2007 |
| WO | 2007115282 | | 10/2007 |
| WO | 2008011363 | A2 | 1/2008 |
| WO | 2009002145 | A1 | 12/2008 |
| WO | 2010021766 | A1 | 2/2010 |
| WO | 2011082111 | A1 | 7/2011 |
| WO | 2012071459 | | 5/2012 |
| WO | 2015018913 | | 2/2015 |
| WO | 2016149277 | | 9/2016 |
| WO | 2017042198 | | 3/2017 |
| WO | 2017062311 | A1 | 4/2017 |
| WO | 2017109195 | | 6/2017 |
| WO | 2017158132 | | 9/2017 |

OTHER PUBLICATIONS

Pyrone [website: obtained from https://en.wikipedia.org/wiki/Pyrone, last access Feb. 12, 2024] (Year: 2024).*

Spaulding et al. "Nutraceutical and pharmaceutical cocktails did not improve muscle function or reduce histological damage in D2-mdx mice" J Appl Physiol, 2019, vol. 127, pp. 1058-1066.

Ogrodnik et al. "Cellular senescence drives age-dependent hepatic steatosis" Nature Communications, 2017, vol. 8, No. 1, XP55648710.

Liu et al., "Nicotinamide Forestalls Pathology and Cognitive Decline in Alzheimer Mice: Evidence for Improved Neuronal Bioenergetics and Autophagy Procession", Neurobiology of Aging, vol. 34, 2013, pp. 1564-1580, XP028997212.

Office Action Received for Application No. BR112020022985-7, mailed on Apr. 10, 2023, 4 Pages of Official copy.

Office Action Received for Application No. CN201980038137.7, mailed on Mar. 17, 2023, 15 Pages (7 Pages of English Translation and 8 Pages of Official copy).

Lopez, "Mild Cognitive Impairment", Continuum (Minneap Minn), vol. 19, Issue No. 2, 2013, pp. 411-424.

"Dementia—Symptoms and Causes", Mayo Clinic, Retrieved from URL: <https://www.mayoclinic.org/diseases-conditions/dementia/symptoms-causes/syc-20352013>, Nov. 28, 2023, p. 1-4.

"Mild Cognitive Impairment (MCI)—Symptoms and Causes", Mayo Clinic, Retrieved from URL: <https://www.mayoclinic.org/diseases-conditions/mild-cognitive-impairment/symptoms-causes/syc-20354578#:-: text=Overview,mental%20function%20has%20%22slipped.%22>, Nov. 28, 2023, p. 1-2.

Kane et al., "Interventions to Prevent Age-Related Cognitive Decline, Mild Cognitive Impairment, and Clinical Alzheimer's-Type Dementia", Comparative Effectiveness Review, No. 188, Mar. 2017, pp. 1-693.

Oxford English Dictionary, Definition of "to prevent", Retrieved on Dec. 7, 2023, 11 Pages.

Douris et al., "Adaptive Changes in Amino Acid Metabolism Permit Normal Longevity in Mice Consuming a Low-Carbohydrate Ketogenic Diet", Biochimica Et Biophysica Acta, vol. 1852, Issue No. 10, 2015, pp. 2056-2065.

Powanda et al., "Evidence for a Linear Correlation between the Level of Dietary Tryptophan and Hepatic Nad Concentration and for a Systematic Variation in Tissue Nad Concentration in the Mouse and the Rat1", The Journal of Nutrition, vol. 100, Issue No. 12, 1970, pp. 1471-1478.

Pinto et al., "Anti-Oxidant and Anti-Inflammatory Activity of Ketogenic Diet: New Perspectives for Neuroprotection in Alzheimer's Disease", Antioxidants, vol. 7, Issue No. 5, 2018, pp. 1-16.

Porter et al., "Effects of Acute Tryptophan Depletion on Cognitive Function in Alzheimer's Disease and in the Healthy Elderly", Psychological Medicine, vol. 33, Issue No. 1, 2003, pp. 41-49.

Cunnane et al., "Can Ketones Compensate for Deteriorating Brain Glucose uptake during Aging? Implications for the Risk and Treatment of Alzheimer's Disease", Annals of the New York Academy of Sciences, vol. 1367, Issue No. 1, 2016, pp. 12-20.

Elamin et al., "Ketone-Based Metabolic Therapy: is Increased Nad+ a Primary Mechanism?", Frontiers in Molecular Neuroscience, vol. 10, 2017, pp. 1-9.

Yang et al., "NAD+ Metabolism: Bioenergetics, Signaling and Manipulation for Therapy", Biochimica et Biophysica Acta, vol. 1864, Issue No. 12, 2016, pp. 1-31.

"Blue Raspberry Flavoured Pre-Exertion Performance Optimizer", Mintel, Record Id 5515873, Apr. 2018, 3 Pages.

Australian Office Action for Appl No. 2019290926 dated Aug. 26, 2024, 5 pages.

Liu et al., "Apolipoprotein E and Alzheimer Disease: Risk, Mechanisms, and Therapy", Nature Reviews. Neurology Reviews. Neurology, vol. 9, Issue No. 2, 2013, pp. 1-27.

Fukuwatari et al., "Effect of Nicotinamide Administration on the Tryptophan-nicotinamide Pathway in Humans", International Journal for Vitamin and Nutrition Research, vol. No. 77, Issue No. 4, 2007, pp. 255-262.

The National Academies Press, "Dietary Reference Intakes for Thiamin, Riboflavin, Niacin, Vitamin B6, Folate, Vitamin B12, Pantothenic ACID, Biotin, and Choline", Retrieved From: "https://www.nationalacademies.org/read/6015/chapter/8#125", 1998, Chapter: 6 Niacin, 592 Pages.

Examination Report No. 2 for corresponding Australian Patent Application No. 2025200329, dated Mar. 17, 2026. 4 pages.

European Office Action for Appl No. 19 726 395.7-1109 dated Apr. 1, 2026, 7 pages.

Office Action issued by the European Patent Office for Application No. 19728593.5-1109 dated Apr. 1, 2026, 14 pages.

European Office Action for Appl No. 19 728 593.5-1109 dated Jun. 16, 2025, 12 pages.

Guillemin et al., "Kynurenine Pathway Metabolism in Human Astrocytes: A Paradox for Neuronal Protection", Journal of Neurochemistry, vol. 78, 2001, pp. 842-853.

(56) References Cited

OTHER PUBLICATIONS

Schwarcz et al., "The Kynurenine Pathway and the Brain: Challenges, Controversies and Promises", Neuropharmacology, vol. 112, 2017, pp. 1-26.

Australian Office Action for Appl No. 111335AUP01 dated Jul. 3, 2026, 5 pages.

* cited by examiner

COMPOSITIONS AND METHODS USING A NICOTINAMIDE ADENINE DINUCLEOTIDE (NAD+) PRECURSOR AND AT LEAST ONE KETONE OR KETONE PRECURSOR

CROSS REFERENCE TO RELATED APPLICATIONS

The present application is a National Stage of International Application No. PCT/EP2019/063425, filed on May 24, 2019, which claims priority to U.S. Provisional Patent Application No. 62/688,045, filed on Jun. 21, 2018, the entire contents of which are being incorporated herein by reference.

BACKGROUND

The present disclosure generally relates to compositions and methods that can treat or prevent oxidative stress, a condition associated with oxidative stress, a reduced level of glutathione, a condition associated with a reduced level of glutathione, a reduced redox ratio $NAD^+/NADH$, or a condition associated with lower redox ratio $NAD^+/NADH$. Alternatively or additionally, the compositions and the methods can improve exercise capacity and physical function.

During the past decades, the prevalence of obesity has increased worldwide to epidemic proportion. Approximately 1 billion of people worldwide are overweight or obese, conditions that increase mortality, mobility and economical costs. Obesity develops when energy intake is greater than energy expenditure, the excess energy being stored mainly as fat in adipose tissue. Body weight loss and prevention of weight gain can be achieved by reducing energy intake or bioavailability, increasing energy expenditure, and/or reducing storage as fat.

In addition, population aging has been a remarkable demographic event. As the growth of the older population has outpaced the total population due to increased longevity, the proportion of older persons relative to the rest of the population has increased considerably due to decreased fertility rates. For example, one in every twelve individuals was at least 60 years of age in 1950, and one in every ten was aged 60 years or older by the end of 2000. By the end of 2050, the number of persons worldwide that is 60 years or over is projected to be one in every five.

Aged or aging individuals frequently suffer some degree of cognitive impairment, including decline in cognitive function, that progresses with age, and age-related changes in brain morphology and cerebrovascular function are commonly observed. Cognitive decline has been consistently reported with aging across a range of cognitive domains including processing speed, attention, episodic memory, spatial ability and executive function. Brain imaging studies have revealed that these normal age-related cognitive declines are associated with decreases in both grey and white matter volume in the brain, with the fronto-striatal system most heavily compromised with aging. These decreases in cortical volume can be attributed to a number of detrimental cellular processes involved with normal aging, such as accumulation of damage by free radicals over time leading to oxidative damage, chronic low-grade inflammation, homocysteine accumulation (which when elevated are a risk factor for cognitive impairment and dementia), and decreased mitochondrial efficiency. In addition to direct cellular damage, the brain is also indirectly impaired by insults to micro-vascular structures. It is evident that the pathology of aging and also dementia involves a complexity of these interacting factors which are linked together. For example, mitochondrial dysfunction leads to increased oxidative stress, and oxidative stress can trigger inflammation and vascular insults.

Furthermore, cognitive decline is an early predictor or Alzheimer pathology and begins before the onset of dementia. In this context, the cognitive composite score represents a reliable means to assess the cognitive decline preceding dementia. Considerable evidence suggests that maintaining brain health and preventing cognitive decline with advancing age may prevent or delay development of dementia due to Alzheimer's disease and other aged related neuropathologies.

Nutrition, education, physical exercise and cognitive exercise have been recently demonstrated as possible intervention to prevent cognitive decline with aging. An abundance of clinical, epidemiological, and individual evidence is in favor of individual nutritional factors that reduce dementia risk and age-related neurodegeneration. However, formal trial testing of nutritional interventions has yielded mixed results (Schmitt et al., Nutrition Reviews 68: S2-S5 (2010).

Another condition adversely affecting some individuals is that their body tissues do not respond properly to insulin. Insulin receptors in the tissues cease to function adequately, and gluco-dependent cells fail to recognize the presence of insulin. As a result, the pancreas needs to secrete more insulin to help glucose enter these cells. The pancreas tries to keep up with this increased demand for insulin by producing more. This phenomenon is called insulin resistance (also known as low insulin sensitivity). Many people with insulin resistance have high levels of both glucose and insulin circulating in their blood at the same time. Eventually, the pancreas fails to keep up with the body's need for insulin, leading to Type II diabetes.

Insulin resistance and Type II diabetes are associated with increased risk of heart attacks, strokes, amputation, diabetic retinopathy, and kidney failure. For extreme cases, circulation of limbs is affected, potentially requiring amputation. Loss of hearing, eyesight, and cognitive ability has also been linked to these conditions.

Management of insulin resistance in children and adults is essentially based on dietary and lifestyle changes, including healthier dietary habits and increased exercise. These practices can be very efficient in improving insulin sensitivity and in slowing the progression of the disease, but they are difficult to apply and actually not followed by most patients. Type II diabetes can be treated with drugs promoting insulin sensitivity, but their efficacy in reducing the rate of progression of the disease is quite low. Insulin treatment is required during the most advanced phases of the disease.

Products containing n-3 polyunsaturated fatty acids, fibers, oligosaccharides and even probiotics have been proposed as nutritional solutions to improve insulin sensitivity and to reduce insulin resistance. However, the efficacy of these nutritional interventions is quite marginal and even controversial, with studies showing no effect or even deleterious effects.

SUMMARY

In an embodiment, the present disclosure provides a method of treating or preventing at least one physical state selected from the group consisting of oxidative stress, a condition associated with oxidative stress, a reduced level of glutathione, a condition associated with a reduced level of glutathione, a lower redox ratio $NAD^+$/NADH, or a condition associated with a lower redox ratio $NAD^+$/NADH. The method comprises administering to an individual in need thereof an effective amount of a combination of a Nicotinamide Adenine Dinucleotide ($NAD^+$) precursor and at least one ketone or ketone precursor.

In an embodiment, the at least one physical state is selected from the group consisting of deleterious effects of aging, muscle loss, type I diabetes, type II diabetes, complications from diabetes, insulin resistance, metabolic syndrome, dyslipidemia, overweight, obesity, raised cholesterol levels, raised triglyceride levels, elevated fatty acid levels, fatty liver disease, cardiovascular disease, neurodegenerative disease such as Alzheimer's Disease and Parkinson's Disease, depression, anxiety, decreased motivation, impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, HIV infection, stroke, migraine, and brain ischemia.

In an embodiment, the $NAD^+$ precursor is selected from the group consisting of Tryptophan, Nicotinic Acid, Nicotinamide, Nicotinamide Riboside (NR), Reduced Nicotinamide riboside (NRH), Nicotinamide Mononucleotide (NMN), Trigonelline, Nicotinic acid mononucleotide, Nicotinic acid riboside, and mixtures thereof.

In an embodiment, the at least one ketone or ketone precursor is selected from the group consisting of medium chain triglycerides (MCTs), MCT derivatives, ketone esters such as mono-esters (e.g., R-3-hydroxybutyl R-3-hydroxybutyrate) and aceto-acetate diesters (e.g., 1,3-butanediol acetoacetate diester), ketone salts, BHB (β-Hydroxybutyrate), D-BHB salts, β-hydroxypentanoate, β-ketopentanoate, aceto-acetate (AcA) and mixtures thereof.

In an embodiment, the combination is administered orally or enterally, via a nasogastric tube.

In an embodiment, the combination is administered in a composition selected from the group consisting of a food product, a food supplement, an oral nutritional supplements (ONS), a medical food, and combinations thereof.

In an embodiment, at least a portion of the $NAD^+$ precursor is administered in the same composition as at least a portion of the at least one ketone or ketone precursor.

In an embodiment, at least a portion of the $NAD^+$ precursor is administered in a different composition as at least a portion of the at least one ketone or ketone precursor.

In another embodiment, the present disclosure provides a method of delaying off-set of metabolic decline, maintaining muscle mass, decreasing oxidative stress, maintaining immune function and/or maintaining cognitive function in a healthy older adult. The method comprises administering to the healthy older adult an effective amount of a combination of a $NAD^+$ precursor and at least one ketone or ketone precursor. The healthy older adult can be elderly.

In another embodiment, the present disclosure provides a method of enhancing metabolizing of reactive oxygen species, improving glucose control and/or improving muscle function in an individual with at least one of obesity or diabetes. The method comprises administering to the individual an effective amount of a combination of a $NAD^+$ precursor and at least one ketone or ketone precursor.

In another embodiment, the present disclosure provides a method of improving mitochondrial function in an individual with sarcopenia. The method comprises administering to the individual an effective amount of a combination of a $NAD^+$ precursor and at least one ketone or ketone precursor. The individual with sarcopenia can be otherwise healthy.

In another embodiment, the present disclosure provides a method of improving one or more of fetal metabolic programming for prevention of later development of obesity and/or diabetes, maternal and fetal health in gestational diabetes, exercise capacity and physical function, quality of life, longevity, memory, cognition, post-traumatic recovery and survival, or recovery from trauma and surgery. The method comprises administering to an individual an effective amount of a combination of a $NAD^+$ precursor and at least one ketone or ketone precursor. The individual can have at least one of impaired cognitive function or a cognitive disorder, and the composition can comprise an amount of the combination effective to improve cognition. The individual can not have impaired cognitive function or a cognitive disorder, and the composition can comprise an amount of the combination effective to improve cognition.

In another embodiment, the present disclosure provides a method of improving at least one of muscle performance or muscle recovery from exercise. The method comprises administering to an individual performing the exercise an effective amount of a combination of a $NAD^+$ precursor and at least one ketone or ketone precursor during at least one time selected from the group consisting of before the exercise, during the exercise, and after the exercise.

In another embodiment, the present disclosure provides a composition comprising a combination of a $NAD^+$ precursor and at least one ketone or ketone precursor (e.g., a ketone ester). The composition comprises the combination in an amount effective for at least one of (i) treating or preventing at least one physical state selected from the group consisting of oxidative stress, a condition associated with oxidative stress, a reduced level of glutathione, a condition associated with a reduced level of glutathione, or (ii) improving one or more of fetal metabolic programming for prevention of later development of obesity and/or diabetes, maternal and fetal health in gestational diabetes, exercise capacity and physical function, quality of life, longevity, memory, cognition, post-traumatic recovery and survival, or recovery from trauma and surgery.

In an embodiment, the amount of the combination is effective to treat or prevent at least one physical state selected from the group consisting of deleterious effects of aging, muscle loss, type I diabetes, type II diabetes, complications from diabetes, insulin resistance, metabolic syndrome, dyslipidemia, overweight, obesity, raised cholesterol levels, raised triglyceride levels, elevated fatty acid levels, fatty liver disease, cardiovascular disease, neurodegenerative disease such as Alzheimer's Disease and Parkinson's Disease, depression, anxiety, decreased/low motivation, impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, HIV infection stroke, migraine, and brain ischemia.

In an embodiment, the composition is selected from the group consisting of a food product, a food supplement, an oral nutritional supplements (ONS), a medical food, and combinations thereof.

An advantage of one or more embodiments provided by the present disclosure is to potentiate benefits on oxidative metabolism and prevent DNA damage.

Another advantage of one or more embodiments provided by the present disclosure is to replenish $NAD^+$ pools, which decline with age.

Yet another advantage of one or more embodiments provided by the present disclosure is to help off-set slowing of the metabolism associated with aging.

Another advantage of one or more embodiments provided by the present disclosure is to help increase fatty acids metabolism.

Yet another advantage of one or more embodiments provided by the present disclosure is to help the body to metabolize fat and increase lean body mass.

An advantage of one or more embodiments provided by the present disclosure is to help maintain heart health.

Another advantage of one or more embodiments provided by the present disclosure is to help support healthy LDL-cholesterol and fatty acid levels in the blood.

Yet another advantage of one or more embodiments provided by the present disclosure is to supplement key amino acids which become less available in cells in sufficient quantities during aging.

An advantage of one or more embodiments provided by the present disclosure is to enhance production of Glutathione, which is important for cellular function.

Another advantage of one or more embodiments provided by the present disclosure is to help increase Glutathione levels within cells.

Yet another advantage of one or more embodiments provided by the present disclosure is to improve concentration of Glutathione levels which decline with age.

An advantage of one or more embodiments provided by the present disclosure is to help maintain healthy muscle mass.

Another advantage of one or more embodiments provided by the present disclosure is to help reduce oxidative stress on the body.

Yet another advantage of one or more embodiments provided by the present disclosure is to support a normal immune system via Glutathione modulation.

Additional features and advantages are described in, and will be apparent from, the following Detailed Description and the Figures.

DETAILED DESCRIPTION

Definitions

Figure 1:
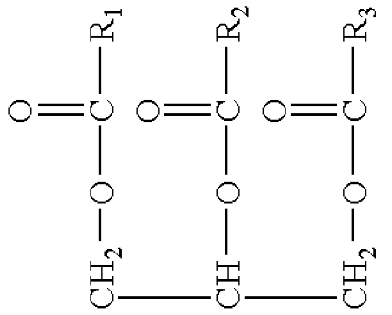
FIGS. 1-5 each show chemical formulas for non-limiting examples of ketone precursors suitable for the compositions and methods disclosed herein.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +10% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y." For example, "at least one ketone or ketone precursor" should be interpreted as "a ketone" or "a ketone precursor," or "both a ketone and a ketone precursor."

Where used herein, the terms "example" and "such as," particularly when followed by a listing of terms, are merely exemplary and illustrative and should not be deemed to be exclusive or comprehensive. As used herein, a condition "associated with" or "linked with" another condition means the conditions occur concurrently, preferably means that the conditions are caused by the same underlying condition, and most preferably means that one of the identified conditions is caused by the other identified condition.

The terms "food," "food product" and "food composition" mean a product or composition that is intended for ingestion by an individual such as a human and provides at least one nutrient to the individual. A food product typically includes at least one of a protein, a lipid, a carbohydrate and optionally includes one or more vitamins and minerals. The compositions of the present disclosure, including the many embodiments described herein, can comprise, consist of, or consist essentially of the elements disclosed herein, as well as any additional or optional ingredients, components, or elements described herein or otherwise useful in a diet.

As used herein, the term "isolated" means removed from one or more other compounds or components with which the compound may otherwise be found, for example as found in nature. For example, "isolated" preferably means that the identified compound is separated from at least a portion of the cellular material with which it is typically found in nature. In an embodiment, an isolated compound is pure, i.e., free from any other compound.

"Prevention" includes reduction of risk, incidence and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The term "unit dosage form", as used herein, refers to physically discrete units suitable as unitary dosages for human and animal subjects, each unit containing a predetermined quantity of the composition disclosed herein in an amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

A "subject" or "individual" is a mammal, preferably a human. It can also be an animal, in particular a pet. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

As used herein, an "effective amount" is an amount that prevents a deficiency, treats a disease or medical condition in an individual, or, more generally, reduces symptoms, manages progression of the disease, or provides a nutritional, physiological, or medical benefit to the individual. The relative terms "improved," "increased," "enhanced" and the like refer to the effects of the composition disclosed herein, namely a composition comprising a combination of a $NAD^+$ precursor and at least one ketone or ketone precursor (e.g., a ketone ester), relative to a composition not having this combination. As used herein, "promoting" refers to enhancing or inducing relative to the level before administration of the composition disclosed herein.

"Sarcopenia" is defined as the age-associated loss of muscle mass and functionality (including muscle strength and gait speed). As used herein, "frailty" is defined as a clinically recognizable state of increased vulnerability resulting from aging-associated decline in reserve and function across multiple physiologic systems such that the ability to cope with everyday or acute stressors is compromised. In the absence of an established quantitative standard, frailty has been operationally defined by Fried et al. as meeting three out of five phenotypic criteria indicating compromised energetics: (1) weakness (grip strength in the lowest 20% of population at baseline, adjusted for gender and body mass index), (2) poor endurance and energy (self-reported exhaustion associated with $VO_2$ max), (3) slowness (lowest 20% of population at baseline, based on time to walk 15 feet, adjusting for gender and standing height), (4) low physical activity (weighted score of kilocalories expended per week at baseline, lowest quintile of physical activity identified for each gender; e.g., less than 383 kcal/week for males and less than 270 kcal/week for females), and/or unintentional weight loss (10 lbs. in past year). Fried L P, Tangen C M, Walston J, et al., "Frailty in older adults: evidence for a phenotype." J. Gerontol. A. Biol. Sci. Med. Sci. 56(3): M146-M156 (2001). A pre-frail stage, in which one or two of these criteria are present, identifies a high risk of progressing to frailty.

"Cachexia" is a severe body wasting condition characterized by marked weight loss, anorexia, asthenia, and anaemia. Cachexia is a common feature of a number of illnesses, such as cancer, sepsis, chronic heart failure, rheumatoid arthritis, and acquired immune deficiency syndrome (AIDS).

"Overweight" is defined for a human as a body mass index (BMI) between 25 and 30 kg/m$^2$. "Obese" is defined for a human as a BMI of at least 30 kg/m$^2$, for example 30-39.9 kg/m$^2$. "Weight loss" is a reduction of the total body weight. Weight loss may, for example, refer to the loss of total body mass in an effort to improve one or more of health, fitness or appearance.

"Diabetes" encompasses both the type I and type II forms of the disease. Non-limiting examples of risk factors for diabetes include: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

As used herein, the term "metabolic syndrome" refers to a combination of medical disorders that, when occurring together, increase the risk of developing cardiovascular disease and diabetes. It affects one in five people in the United States and prevalence increases with age. Some studies have shown the prevalence in the United States to be an estimated 25% of the population. In accordance with the International Diabetes Foundation consensus worldwide definition (2006), metabolic syndrome is central obesity plus any two of the following:

- Raised triglycerides: >150 mg/dL (1.7 mmol/L), or specific treatment for this lipid abnormality;
- Reduced HDL cholesterol: <40 mg/dL (1.03 mmol/L) in males, <50 mg/dL (1.29 mmol/L) in females, or specific treatment for this lipid abnormality;
- Raised blood pressure: systolic BP>130 or diastolic BP>85 mm Hg, or treatment of previously diagnosed hypertension; and
- Raised fasting plasma glucose: (FPG)>100 mg/dL (5.6 mmol/L), or previously diagnosed type 2 diabetes.

As used herein, "neurodegenerative disease" or "neurodegenerative disorder" refers to any condition involving progressive loss of functional neurons in the central nervous system. In an embodiment, the neurodegenerative disease is associated with age-related cell death. Non-limiting examples of neurodegenerative diseases include Alzheimer's disease, Parkinson's disease, Huntington's disease, amyotrophic lateral sclerosis (also known as ALS and as Lou Gehrig's disease), AIDS dementia complex, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Kennedy's disease, Krabbe disease, Lyme disease, Machado-Joseph disease, multiple sclerosis, multiple system atrophy, neuroacanthocytosis, Niemann-Pick disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome. The present disclosure is not limited to a specific embodiment of the neurodegenerative disease, and the neurodegenerative disease can be any neurologically-related condition known to one skilled in this art.

As used herein, "cognitive function" refers to any mental process that involves symbolic operations, e.g., perception, memory, attention, speech comprehension, speech generation, reading comprehension, creation of imagery, learning, and reasoning, preferably at least memory.

Methods for measuring cognitive function are well-known and can include, for example, individual or battery tests for any aspect of cognitive function. One such test is the Prudhoe Cognitive Function Test by Margallo-Lana et al. (2003) J. Intellect. Disability Res. 47:488-492. Another such test is the Mini Mental State Exam (MMSE), which is designed to assess orientation to time and place, registration, attention and calculation, recall, language use and comprehension, repetition, and complex commands. Folstein et al. (1975) J. Psych. Res. 12:189-198. Such tests can be used to assess cognitive function in an objective manner, so that changes in cognitive function, for example in response to treatment in accordance with methods disclosed herein, can be measured and compared.

As used herein, a "cognitive disorder" refers to any condition that impairs cognitive function. Non-limiting examples of a cognitive disorder include delirium, dementia, learning disorder, attention deficit disorder (ADD), and attention deficit hyperactivity disorder (ADHD).

A triglyceride (also known as a triacylglycerol or a triacylglyceride) is an ester that is derived from glycerol and three fatty acids. Fatty acids may be either unsaturated or saturated. Fatty acids which are not attached to other molecules are referred to as free fatty acids (FFA).

A medium-chain triglyceride (MCT) is a triglyceride in which all three fatty acid moieties are medium-chain fatty acid moieties. As defined herein, medium-chain fatty acids (MCFA) are fatty acids that have 6 to 12 carbon atoms.

EMBODIMENTS

The present disclosure provides compositions comprising a combination of a NAD precursor and at least one ketone or ketone precursor (e.g., a ketone ester). In an embodiment, the $NAD^+$ precursor is selected from the group consisting of Tryptophan, Nicotinic Acid (Niacin), Nicotinamide (Niacinamide), Nicotinamide Riboside (NR), Reduced Nicotinamide Riboside (NRH), Beta-Nicotinamide Mononucleotide (NMN), Trigonelline (N-Methylnicotinate), Nicotinic acid mononucleotide, Nicotinic acid riboside, a food extract enriched in at least one of these compounds, e.g., a food extract enriched in Nicotinamide adenine dinucleotide (NAD), and mixtures thereof. As used herein, "nicotinamide riboside" includes L-valine and L-phenylalanine esters of nicotinamide riboside.

Figure 2:
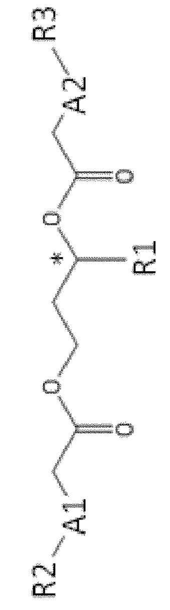
Figure 3:
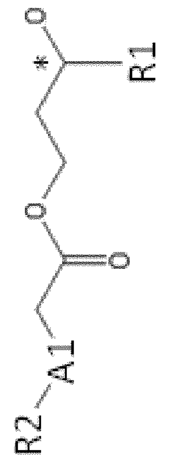
Figure 4:
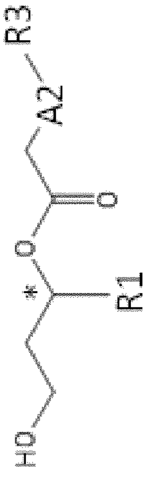

In an embodiment, the at least one ketone or ketone precursor comprises a medium chain triglyceride where the residues R1, R2 and R3 are independently an aliphatic linear chain containing 7-carbon, 8-carbon, 9-carbon, or 10-carbon (FIG. 1). In an embodiment, the at least one ketone or ketone precursor comprises a ketone ester where R1, R2, R3 is a methyl residue and A1 and A2 are independently either $CH_2$, CHOH or C═O, and * is either the R or S enantiomer, or both (FIGS. 2-4).

Figure 5:
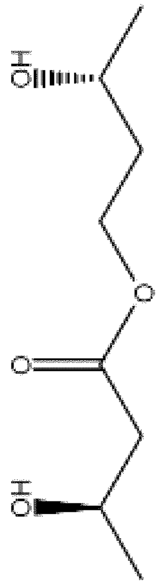

In an embodiment, the at least one ketone or ketone precursor is selected from the group consisting of medium chain triglycerides (MCTs); MCT derivatives; ketone esters such as mono-esters (e.g., (R)-3-hydroxybutyl-(R)-3-hydroxybutyrate (FIG. 5)) and aceto-acetate diesters (e.g., R,S-1,3-butanediol acetoacetate diester; ketone salts; BHB (β-Hydroxybutyrate) and salts thereof such as sodium salts, magnesium salts, potassium salts, calcium salts and combinations thereof; D-BHB and salts thereof such as sodium salts, magnesium salts, potassium salts, calcium salts and combinations thereof; β-hydroxypentanoate and salts thereof such as sodium salts, magnesium salts, potassium salts, calcium salts and combinations thereof; D-β-hydroxypentanoate and salts thereof such as sodium salts, magnesium salts, potassium salts, calcium salts and combinations thereof; β-ketopentanoate and salts thereof such as sodium salts, magnesium salts, potassium salts, calcium salts and combinations thereof; hexanoyl ethyl β-hydroxybutyrate; octanoyl ethyl β-hydroxybutyrate; hexanoyl hexyl β-hydroxybutyrate; aceto-acetate (AcA) and salts thereof such as sodium salts, magnesium salts, potassium salts, calcium salts and combinations thereof; and mixtures thereof. MCTs comprise three fatty acid moieties, each of which independently has between 6-12, 6-11, 6-10, 7-12, 7-11, 7-10, 8-12, 8-11 or 8-10 carbon atoms.

Each of the compounds can be administered at the same time as the other compounds (i.e., as a single unit) or separated by a time interval (i.e., in separate units). The present disclosure further provides a kit comprising a $NAD^+$ precursor and at least one ketone or ketone precursor (e.g., a ketone ester) for admixing to form one or more of the compositions disclosed herein and/or for use in one or more of the methods disclosed herein, for example in separate containers as two or more liquid solutions or dried powders. In some embodiments, one or more of these compounds can be isolated compounds.

Accordingly, an aspect of the present disclosure is a composition comprising a combination of a $NAD^+$ precursor and at least one ketone or ketone precursor (e.g., a ketone ester), the composition containing the combination in an amount effective for treatment or prevention of at least condition selected from the group consisting of deleterious effects of aging, muscle loss (for any reason, including at least sarcopenia, HIV infection, aging, cachexia, deleterious effects of weightlessness), diabetes (type I or type II), complications from diabetes (e.g., diabetic dyslipidemia and/or diabetic microvascular complications such as nephropathy, retinopathy, and/or neuropathy), insulin resistance, metabolic syndrome, dyslipidemia, overweight, obesity, raised cholesterol levels, raised triglyceride levels, elevated fatty acid levels, fatty liver disease (e.g., non-alcoholic fatty liver disease, including with or without inflammation), cardiovascular disease (e.g., heart failure and/or impaired cardiac contractile function), neurodegenerative disease (e.g., from aging), depression, anxiety, decreased/low motivation, impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress (e.g., from burns or trauma), traumatic brain injury (including concussions), cystic fibrosis, inflammation, cancer, HIV infection stroke, migraine, and brain ischemia.

For example, aging is a condition that can be linked to one of the following: oxidative stress, reduced level of glutathione, lower redox ratio $NAD^+/NADH$. The compositions disclosed herein can treat or prevent these deleterious effects of aging.

As other examples, depression is linked to low glutathione, and anxiety is linked to oxidative stress. The compositions disclosed herein can treat or prevent these conditions.

Another aspect of the present disclosure is a method of treating at least one of these conditions, the method comprising administering to the individual a composition comprising a therapeutically effective amount of a combination of a $NAD^+$ precursor and at least one ketone or ketone precursor (e.g., a ketone ester). Another aspect of the present disclosure is a method of preventing at least one of these conditions, the method comprising administering to an individual at risk of the at least one condition a composition comprising a prophylactically effective amount of a combination of a $NAD^+$ precursor and at least one ketone or ketone precursor (e.g., a ketone ester).

The composition can treat or prevent sarcopenia, sarcopenic obesity, or cachexia, for example cachexia from an underlying medical condition such as chronic illness, HIV, cancer, chronic obstructive pulmonary disease (COPD), and/or aging in otherwise healthy individuals.

The composition can treat or prevent an eye condition resulting directly or indirectly from low GSH levels, including low levels in the lens of the eye that is known for being rich in glutathione. Non-limiting examples of such conditions include cataracts and/or glaucoma, presbyopia (loss of near vision with aging requiring reading glasses), and presbyacusis (loss of hearing with aging, which requires a hearing aid).

In an embodiment, the composition improves at least one of muscle performance or muscle recovery, such as from muscle stress, including muscle stress associated with exercise. The exercise may be of any kind, including aerobic ("cardio") exercise and/or weight training, for example. The composition can be administered during at least one time selected from the group consisting of before the exercise (e.g., less than one hour before), during the exercise, and after the exercise (e.g., less than one hour after the exercise).

Yet another aspect of the present disclosure is a method of delaying off-set of metabolic decline, maintaining muscle mass, decreasing oxidative stress, maintaining immune function and/or maintaining cognitive function in a healthy older adult. The method comprises administering to the healthy older adult an effective amount of a combination of a $NAD^+$ precursor and at least one ketone or ketone precursor (e.g., a ketone ester).

Another aspect of the present disclosure is a method of improving mitochondrial function in an individual with sarcopenia. The method comprises administering to the individual an effective amount of a combination of a $NAD^+$ precursor and at least one ketone or ketone precursor (e.g., a ketone ester).

Yet another aspect of the present disclosure is a method of enhancing metabolizing of reactive oxygen species, improving glucose control and/or improving muscle function in an individual with at least one of obesity or diabetes. The method comprises administering to the individual an effective amount of a combination of a $NAD^+$ precursor and at least one ketone or ketone precursor (e.g., a ketone ester).

Another aspect of the present disclosure is a method of improving mitochondrial function (preferably to benefit at least one of metabolism or strength) in an individual with sarcopenia. The method comprises administering to the individual an effective amount of a combination of a $NAD^+$ precursor and at least one ketone or ketone precursor (e.g., a ketone ester).

Yet another aspect of the present disclosure is a composition comprising a combination of a $NAD^+$ precursor and at least one ketone or ketone precursor (e.g., a ketone ester), and the composition contains the combination in an amount effective for weight management. "Weight management" for an adult (e.g., at least eighteen years from birth) means that the individual has approximately the same body mass index (BMI) after one week of consumption of the composition, preferably after one month of consumption of the composition, more preferably after one year of consumption of the composition, relative to their BMI when consumption of the composition was initiated. "Weight management" for younger individuals means that the BMI is approximately the same percentile relative to an individual of a corresponding age after one week of consumption of the composition, preferably after one month of consumption of the composition, more preferably after one year of consumption of the composition, relative to their BMI percentile when consumption of the composition was initiated.

In a related embodiment, a method of weight management in an individual comprises administering to the individual a composition comprising an effective amount of a combination of a $NAD^+$ precursor and at least one ketone or ketone precursor (e.g., a ketone ester).

In another aspect, the present disclosure provides a method of improving cognitive function. The method comprises administering to an individual an effective amount of a combination of a $NAD^+$ precursor and at least one ketone or ketone precursor (e.g., a ketone ester). The cognitive function can be selected from the group consisting of perception, memory, attention, speech comprehension, speech generation, reading comprehension, creation of imagery, learning, reasoning, and combinations thereof. In an embodiment, the individual does not have a cognitive disorder; alternatively, the individual has a cognitive disorder. The individual can be elderly and/or can have cognitive decline associated with aging.

Yet another aspect of the present disclosure is a method of improving one or more of fetal metabolic programming for prevention of later development of obesity and/or diabetes, maternal and fetal health in gestational diabetes, exercise capacity and physical function, quality of life, longevity, memory, cognition, post-traumatic recovery and survival (e.g., post-surgical, post-sepsis, post-blunt or penetrating trauma due to accident or physical assault), or recovery from trauma and surgery. The method comprises administering to the individual an effective amount of a combination of a $NAD^+$ precursor and at least one ketone or ketone precursor (e.g., a ketone ester).

In each of the compositions and methods disclosed herein, the composition is preferably a food product, including food additives, food ingredients, functional foods, dietary supplements, medical foods, nutraceuticals, oral nutritional supplements (ONS) or food supplements.

The composition can be administered at least one day per week, preferably at least two days per week, more preferably at least three or four days per week (e.g., every other day), most preferably at least five days per week, six days per week, or seven days per week. The time period of administration can be at least one week, preferably at least one month, more preferably at least two months, most preferably at least three months, for example at least four months. In an embodiment, dosing is at least daily; for example, a subject may receive one or more doses daily. In some embodiments, the administration continues for the remaining life of the individual. In other embodiments, the administration occurs until no detectable symptoms of the medical condition remain. In specific embodiments, the administration occurs until a detectable improvement of at least one symptom occurs and, in further cases, continues to remain ameliorated.

The compositions disclosed herein may be administered to the subject enterally, e.g., orally, or parenterally. Non-limiting examples of parenteral administration include intravenously, intramuscularly, intraperitoneally, subcutaneously, intraarticularly, intrasynovially, intraocularly, intrathecally, topically, and inhalation. As such, non-limiting examples of the form of the composition include natural foods, processed foods, natural juices, concentrates and extracts, injectable solutions, microcapsules, nano-capsules, liposomes, plasters, inhalation forms, nose sprays, nosedrops, eyedrops, sublingual tablets, and sustained-release preparations.

The compositions disclosed herein can use any of a variety of formulations for therapeutic administration. More particularly, pharmaceutical compositions can comprise appropriate pharmaceutically acceptable carriers or diluents and may be formulated into preparations in solid, semi-solid, liquid or gaseous forms, such as tablets, capsules, powders, granules, ointments, solutions, suppositories, injections, inhalants, gels, microspheres, and aerosols. As such, administration of the composition can be achieved in various ways, including oral, buccal, rectal, parenteral, intraperitoneal, intradermal, transdermal, and intratracheal administration. The active agent may be systemic after administration or may be localized by the use of regional administration, intramural administration, or use of an implant that acts to retain the active dose at the site of implantation.

In pharmaceutical dosage forms, the compounds may be administered as their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose functional derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in an aerosol formulation to be administered by inhalation. For example, the compounds can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds can be administered rectally by a suppository. The suppository can include a vehicle such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition. Similarly, unit dosage forms for injection or intravenous administration may comprise the compounds in a composition as a solution in sterile water, normal saline or another pharmaceutically acceptable carrier, wherein each dosage unit, for example, mL or L, contains a predetermined amount of the composition containing one or more of the compounds.

Example

The following non-limiting example presents scientific data developing and supporting the concept of a composition comprising a combination of a Nicotinamide Adenine Dinucleotide ($NAD^+$) precursor and at least one ketone or ketone precursor for cellular nutrition.

Method:

Differentiated human iPSC astrocytes were obtained from Cellular Dynamics International (CDI, Madison, WI, USA). The cells were thawed according to the manufacturer's instructions. iCell astrocytes were cultured in DMEM supplemented with 10% fetal calf serum and N2 complement.

Oxygen consumption in human iPSC-derived astrocytes was measured in a Seahorse XF96 instrument (Seahorse Bioscience, North Billerica, MA, USA). Astrocytes were seeded directly into Seahorse 96-well tissue culture plates (XF96 FluxPaks no. 102416-100; Seahorse Bioscience) at a density of 40,000 cells per well. Cells were incubated for 24 hours with 0.5 mM of Nicotinamide riboside chloride (NR) or fresh medium before experiment. Four days after seeding, the cells were washed twice in KRBH 1 mM glucose and incubated for 1 h with the ketone bodies BHB (racemic (D,L) BHB) or BHP (D BHP) at the concentration indicated. The cells were maintained at 37° C. during the experiment. Mitochondrial respiration rates were determined every 6 minutes. Respiratory chain inhibitors were added at the following final concentrations: complex V inhibitor Oligomycin (2.5 μg/ml), complex I inhibitor rotenone (Rot; 1 μM), complex III inhibitor antimycin A (1 μg/ml), and the protonophore FCCP (1 μM).

Summary of the Results:

The oxygen consumption rate in hiPSC-derived astrocytes was measured as an indication of mitochondrial function, using a Seahorse instrument. Through addition of the uncoupling agent FCCP, uncoupled (=maximal) respiration was determined.

Figure 6:
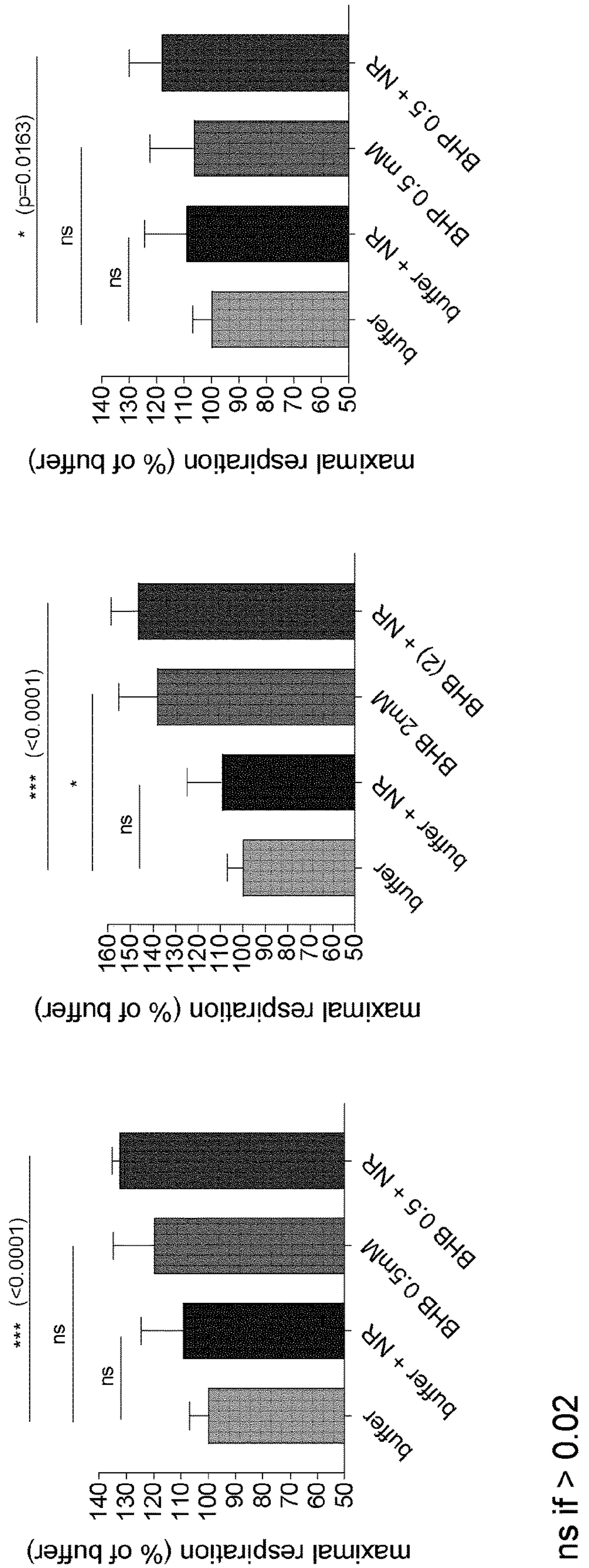
FIG. 6 shows oxygen consumption in human iPSC-derived astrocytes measured in a Seahorse XF96 instrument for BHB (at 0.5 mM or 2 mM) and for BHP with or without NR.

Neither ketone bodies alone nor NR treatment significantly increases maximal respiration. However, when the two are combined, maximal respiration has a very significant increase (FIG. 6).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating or reducing risk, incidence and/or severity of at least one physical state selected from the group consisting of oxidative stress, a condition associated with oxidative stress, a reduced level of glutathione, and a condition associated with a reduced level of glutathione, the method comprising administering to an individual in need thereof an effective amount of a combination of Nicotinamide Riboside (NR) and β-hydroxypentanoate (BHP) or a salt thereof.

2. The method of claim 1, wherein the at least one physical state comprises deleterious effects of aging.

3. The method of claim 1, wherein the NR and the BHP or a salt thereof are administered in a composition that does not include any medium chain triglycerides (MCTs).

4. The method of claim 1, wherein the combination is administered enterally.

5. The method of claim 1, wherein the combination is administered in a composition selected from the group consisting of a food product, a food supplement, an oral nutritional supplements (ONS), a medical food, and combinations thereof.

6. The method of claim 1, wherein at least a portion of the NR is administered in the same composition as at least a portion of the BHP or a salt thereof.

7. The method of claim 1, wherein at least a portion of the NR is administered in a different composition as at least a portion of the BHP or a salt thereof.

8. A method of delaying off-set of metabolic decline, maintaining muscle mass, decreasing oxidative stress and/or maintaining immune function in a healthy older adult, the method comprising administering to the healthy older adult an effective amount of a combination of Nicotinamide Riboside (NR) and β-hydroxypentanoate (BHP) or a salt thereof.

9. The method of claim 8, wherein the healthy older adult is elderly.

10. A method of enhancing metabolizing of reactive oxygen species, improving glucose control and/or improving muscle function in an individual with at least one of obesity or diabetes, the method comprising administering to the individual an effective amount of a combination of Nicotinamide Riboside (NR) and β-hydroxypentanoate (BHP) or a salt thereof.

11. A method of improving mitochondrial function in an individual with sarcopenia, the method comprising administering to the individual an effective amount of a combination of Nicotinamide Riboside (NR) and β-hydroxypentanoate (BHP) or a salt thereof.

12. The method of claim 11, wherein the individual with sarcopenia is otherwise healthy.

* * * * *